United States Patent
Baynham (10) Patent No.: US 10,226,360 B2
(45) Date of Patent: *Mar. 12, 2019

(54) PLIF HINGED SPACER

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/893,246

(22) Filed: Feb. 9, 2018

(65) Prior Publication Data

US 2018/0228620 A1    Aug. 16, 2018

Related U.S. Application Data (63) Continuation of application No. 15/243,321, filed on Aug. 22, 2016, now Pat. No. 9,889,020, which is a continuation-in-part of application No. 14/214,511, filed on Mar. 14, 2014, now Pat. No. 9,421,111.

(60) Provisional application No. 61/800,739, filed on Mar. 15, 2013.

(51) Int. Cl.
*A61F 2/44* (2006.01)
*A61F 2/30* (2006.01)

(52) U.S. Cl.
CPC .............. *A61F 2/447* (2013.01); *A61F 2/442* (2013.01); *A61F 2/4455* (2013.01); *A61F 2002/30156* (2013.01); *A61F 2002/30373* (2013.01); *A61F 2002/30471* (2013.01); *A61F 2002/30543* (2013.01); *A61F 2002/30579* (2013.01); *A61F 2002/30604* (2013.01); *A61F 2002/30622* (2013.01); *A61F 2002/30626* (2013.01); *A61F 2002/30904* (2013.01); *A61F 2002/4475* (2013.01); *A61F 2310/00017* (2013.01); *A61F 2310/00023* (2013.01)

(58) Field of Classification Search
CPC .. A61F 2/44; A61F 2/4455; A61F 2002/4475; A61F 2002/3093

See application file for complete search history.

(56) References Cited

U.S. PATENT DOCUMENTS

| | | | |
|---|---|---|---|
| 5,653,763 A | 8/1997 | Errico et al. |
| 6,015,436 A | 1/2000 | Schonhoffer |
| 6,090,143 A | 7/2000 | Meriwether et al. |
| 6,120,506 A | 9/2000 | Kohrs et al. |
| 6,562,074 B2 | 5/2003 | Gerbec et al. |
| 6,648,917 B2 | 11/2003 | Gerbec et al. |
| 6,821,298 B1 | 11/2004 | Jackson |
| 7,211,112 B2 | 5/2007 | Baynham et al. |

(Continued)

*Primary Examiner* — Eduardo C Robert
*Assistant Examiner* — Tara R Carter
(74) *Attorney, Agent, or Firm* — McHale & Slavin, P.A.

(57) ABSTRACT

A spinal implant formed from a hinged distractor having an upper and lower support body that is hinged by use of pinions. An insert body is constructed and arranged to slide between the section to expand both in height and width, and to maintain a space therebetween. The insert body includes a leading edge that is tapered to allow ease of insertion. A trailing edge that extends beyond a front edge of the upper support body will cause the insert body to be locked into position. A trailing edge engages the rear of the upper support body to prevent over insertion. A lower surface of the insert body may include locking surfaces.

10 Claims, 11 Drawing Sheets

(56) References Cited

U.S. PATENT DOCUMENTS

| | | |
|---|---|---|
| 7,850,733 B2 | 12/2010 | Baynham et al. |
| 8,273,129 B2 | 9/2012 | Baynham et al. |
| 9,421,111 B2 * | 8/2016 | Baynham ................ A61F 2/447 |
| 9,889,020 B2 * | 2/2018 | Baynham ................ A61F 2/447 |
| 2005/0177235 A1 | 8/2005 | Baynham et al. |

* cited by examiner

PLIF HINGED SPACER

PRIORITY CLAIM

In accordance with 37 C.F.R. 1.76, a claim of priority is included in an Application Data Sheet filed concurrently herewith. Accordingly, the present invention claims priority as a continuation of U.S. patent application Ser. No. 15/243,321, filed Aug. 22, 2016, entitled "PLIF Hinged Spacer", which claims priority as a continuation-in-part of U.S. patent application Ser. No. 14/214,511, filed on Mar. 14, 2014, entitled "PLIF Hinged Spacer", now U.S. Pat. No. 9,421,111, issued on Aug. 23, 2016, which claims priority to U.S. Provisional Patent Application No. 61/800,739, filed on Mar. 15, 2013, entitled "PLIF Hinged Spacer", the contents of which are hereby expressly incorporated herein by reference.

FIELD OF THE INVENTION

This invention relates to the field of orthopedic surgery and, more particularly, to implants to be placed between vertebrae in the spine.

BACKGROUND OF THE INVENTION

Spinal stabilization is one approach to alleviating chronic back pain caused by displaced disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition to or in place of the bone graft material, a spinal implant may be inserted in the intervertebral space.

The conventional surgical approach for stabilization has been posteriorly for ease of access to the spine and to avoid interfering with internal organs and tissue. Usually the implant site is prepared to maintain natural lordosis and to accept a certain sized implant within certain pressure limits. This requires considerable time and skill by the surgeon.

U.S. Pat. No. 5,653,763 discloses an orthopaedic cage device having a rectangular cross-section and an intervertebral space shape conforming structure formed of two opposing shell elements being hinged at one end to form an interior volume therebetween. A threaded shaft is axially disposed in the interior volume and is held in place by a retaining ring slideably mounted at the non-hinged axial end of the device. A nut, being of substantially the same dimension as the maximum cross-section of the interior volume in its initial disposition, is disposed on the threaded shaft such that rotation of the shaft causes the nut to translate axially within the interior volume. This translation causes the nut to engage the tapered surface of the interior volume, which in turn causes the non-hinged end of the device to spread such that the device conforms to the natural space between the vertebral bones and provides for the proper curvature of the spine.

U.S. Pat. No. 6,821,298 discloses a fenestrated, hollow intervertebral cage containing a packed, harvested bone graft for fusing adjacent vertebrae together while maintaining or correcting the angular alignment and balance of the spine. Use of the device for an anterior interbody fusion results in a fused bone segment having a predetermined fixed angular orientation. The apparatus has a cage unit adjustably coupled to an expansion cap, and an adjustable wedge to support the adjacent vertebrae with facing surfaces at a predetermined angle relative to each other. A connecting bolt may be threaded or fixed to the rear of the cage unit.

U.S. Pat. No. 6,562,074 discloses a spinal insert which can be manipulated to adjust the height of the implant through links connected to the upper and lower plates.

U.S. Pat. No. 6,120,506 discloses a lordotic implant and a tap for use in preparing the vertebrae. The implant is designed to be inserted between the non-parallel end plates of adjacent vertebrae and maintain the natural lordotic angle of the spine. This is done through the use of a threaded tapered plug inserted in a tapped hole in the direction required by the lordosis of the spine. The implant is hollow and has radial apertures for accommodating bone graft material.

U.S. Pat. No. 6,015,436 discloses a tubular spinal implant. The implant is hollow and has radial apertures for interbody fusion through bone growth material. The device is placed between adjacent vertebrae with the opposite ends of the tube contacting the opposing vertebrae. The opposite ends are threaded together to form the hollow tube.

U.S. Pat. Nos. 7,211,112; 7,850,733; and 8,273,129 disclose opposing wedge ramps having a main body having upper and lower sections with mating sidewalls relatively movable along an inclined ramp. The inclined ramp forms a wedge movable between inclined sidewalls of the main body sections. The main body sections and the inclined ramp form a hollow cube-shaped structure with common open sides.

SUMMARY OF THE INVENTION

Disclosed is an implant formed from a hinged distractor and an insert body. The hinged distractor has an upper and lower support body that is hinged by use of pinions; the pinions are positioned in slots that allow the upper and lower support body to expand in height. The upper and lower bodies are each constructed from two piece cooperating sections, each having a pinion positioned in a slot to allow expansion in width. The insert body is constructed and arranged to slide between the upper and lower support body to expand and maintain a space between the upper and lower support bodies, both in height and width. The spacer includes a leading edge that is tapered to allow ease of insertion. A trailing edge that extends beyond a front edge of the upper support body will cause the insert body to be locked into position. A trailing edge engages the rear of the upper support body to prevent over insertion. A lower surface of the spacer may include locking surfaces.

Accordingly, it is an objective of the instant invention to teach a posterior surgical approach for placement of a spinal implant for interbody fusion allowing the implant to be inserted through a small incision and increased in size in situ.

Accordingly, it is an objective of the instant invention to teach a posterior surgical approach for placement of a spinal implant for interbody fusion allowing the implant to be inserted through a small incision and increased in size in situ.

Still another objective of the instant invention is to teach a spinal implant for interbody fusion that increases in height in situ.

Still another objective of the instant invention is to teach a spinal implant for interbody fusion that increases in width in situ.

It is yet another objective of the instant invention to teach an implant facilitating interbody fusion through bone graft or an ingrowth-type implant.

Other objectives and advantages of this invention will become apparent from the following description taken in conjunction with any accompanying drawings; wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

The spinal implant 10 is inserted in the intervertebral space to replace damaged, missing or excised disk material. This extended position allows the leading end of the distractor to be inserted in a small intervertebral space without the necessity of excising structurally sound bone.

Referring to FIGS. 1-7 in general, disclosed is an implant 10 formed from a hinged distractor 12 and an insert body 14. The hinged distractor 12 is defined by an upper support body 16 and a lower support body 18 that are hinged together by use of pinions 20 and 22 insertable into apertures 23 and 25. The upper support body 16 is formed from a substantially flat plate having an upper surface 24 to provide a large contact area with the vertebra and a lower surface 19 for use in abutting the insert body 14. The top surface 24 includes contact lands and grooves 26 to provide a better purchase, although other stippled treatment may be employed. The upper support body 16 includes side walls 28 and 30 that are sloped from the front edge 32 to the rear edge 34. The slope of the walls is illustrated by a first height H1 adjacent the proximal end of the plate and a second height H2 adjacent the distal end of the plate, the first height H1 greater than the second height H2.

Similarly, a lower support body 18 has an outer surface 36 to provide a large contact area with the vertebra and an inner surface 37 for use in abutting the insert body 14. The outer surface 36 includes contact lands and grooves 38 to provide a better purchase, although other stippled treatment may be employed. The lower support body 18 is further defined by side walls 42 and 44 that are sloped from the front edge 46 to the rear edge 48. The outer surface 36 is a substantially flat plate to provide a large contact area with the vertebra. The lower and upper support body 18 and 16 are pivotable in relation to increase the distance between the front edges 32 and 46.

The distractor 12 upper support body 16 and lower support body 18 may be made of conventional materials used for surgical implants, such as stainless steel and its many different alloys, titanium, and any other metal with the requisite strength and biologically inert properties. Polymeric materials with adequate strength and biological properties may also be used in the construction of the distractor.

The insert body 14 is constructed and arranged to slide between the upper support body 16 and lower support body 18 to expand and maintain a space between the front edges 32 and 46. The insert body 14 has a leading edge 52 that is tapered to allow ease of insertion with light tamping. The leading edge 52 has a trailing edge 54 that extends beyond the front edge 32 of the upper support body 16, causing the insert body 14 to be locked into position. A trailing edge 56 engages the rear edge 34 of the upper support section 16. Similarly, a lower surface of the insert body 14 may include a leading edge 62 that is tapered to allow ease of insertion. The leading edge 62 has a trailing edge 64 that extends beyond the front edge 46 of the lower support body 18, causing the insert body to be locked into position along the top and bottom. Similarly, a rear trailing edge 66 engages the rear edge 48 of the lower support body 18. The insert body 14 is preferably constructed from polyether ether ketone (PEEK), which is an organic polymer thermoplastic. The distractor and insert body are open to allow placement of bone growth material therein, or otherwise provide quicker fusion to the bone. Shown are aperture 70 in the insert body 14 and aperture 72 in the distractor 12.

Figure 1:
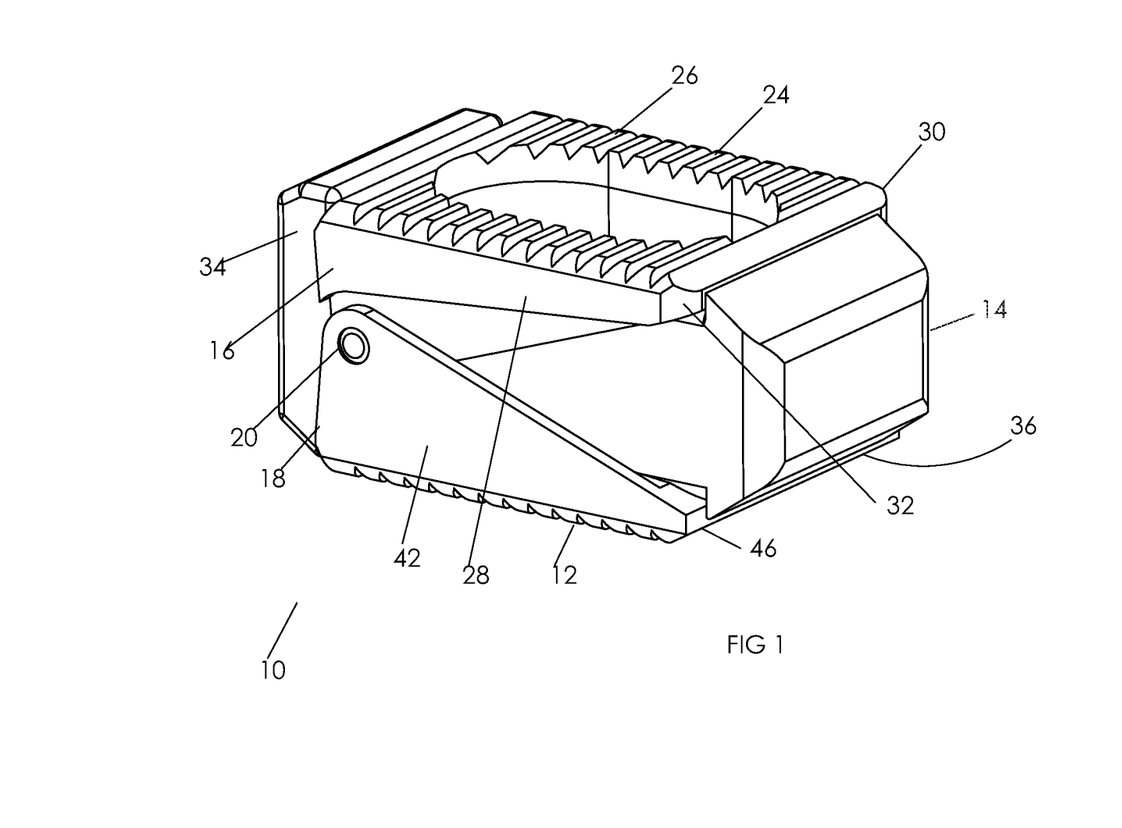
FIG. 1 is a perspective view of the spinal implant.
Figure 2:
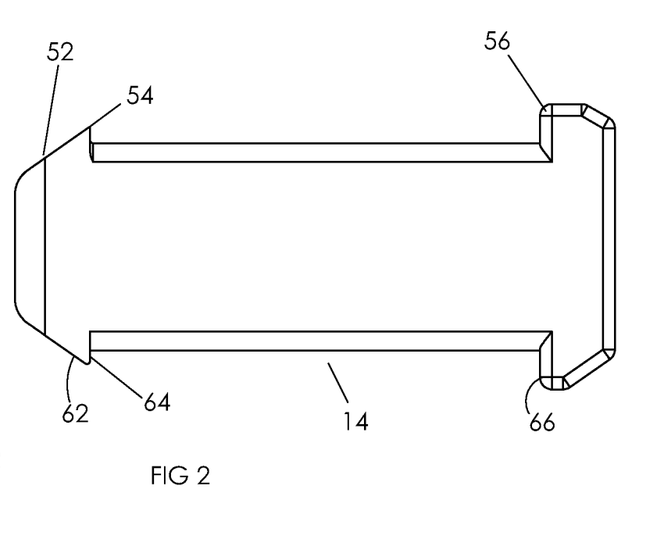
FIG. 2 is an exploded rear view of FIG. 1.
Figure 3:
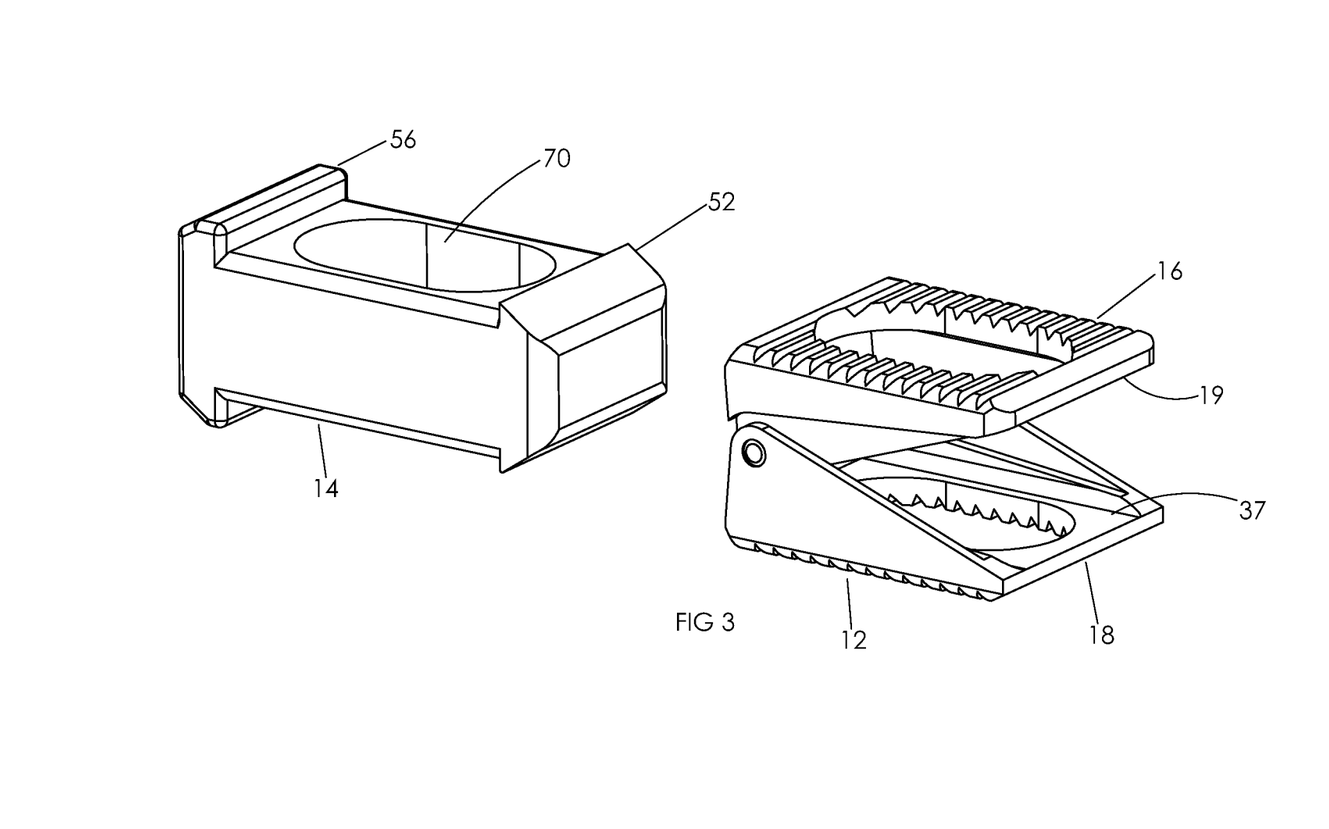
FIG. 3 is a perspective view of the spinal implant with the insert feeding into the distractor.
Figure 4:
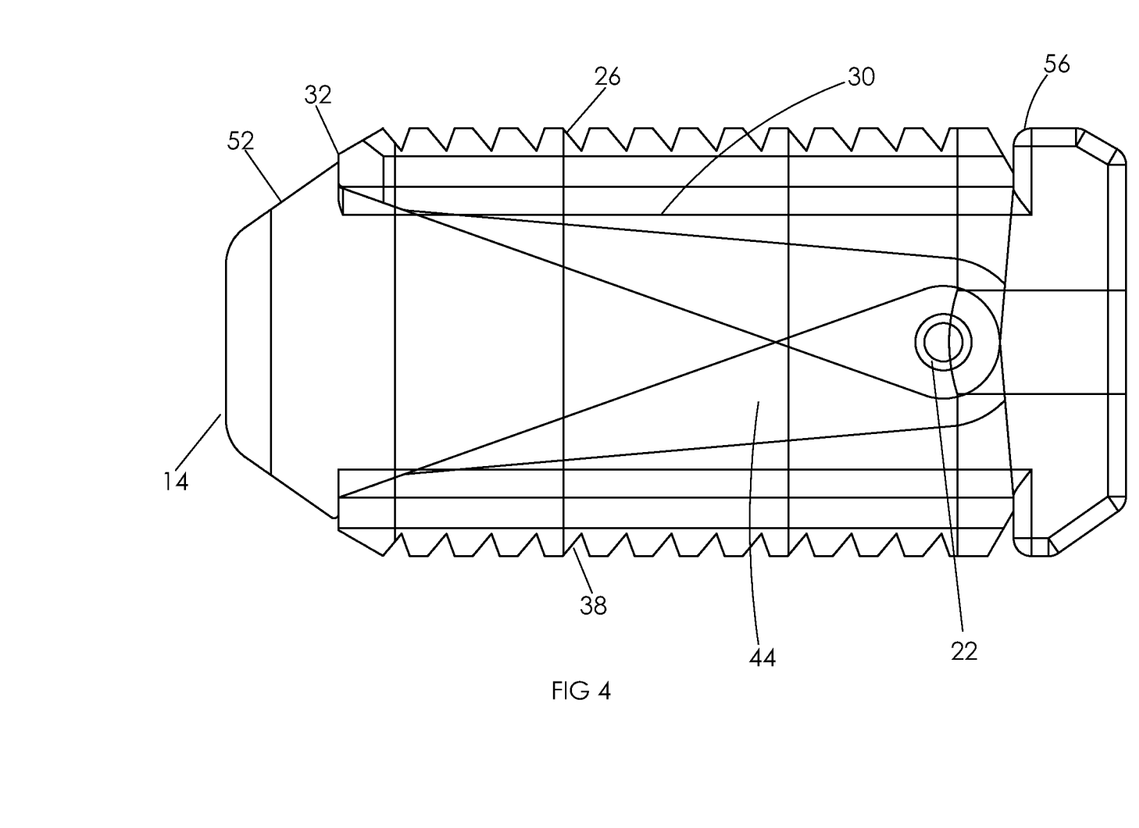
FIG. 4 is a cross sectional side view of the spinal implant.
Figure 5:
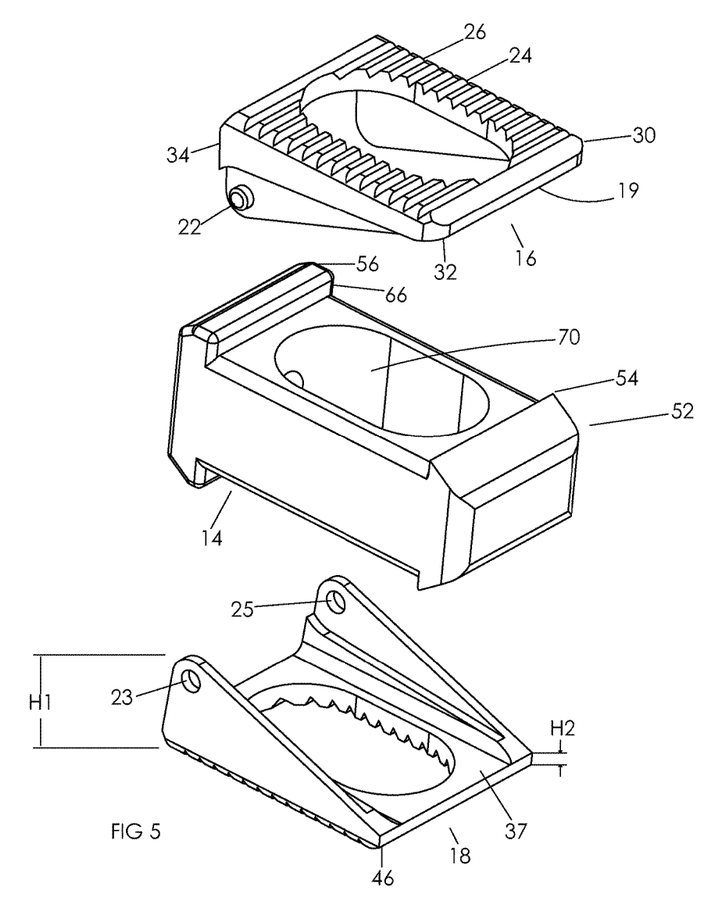
FIG. 5 is an exploded view of the spinal implant.
Figure 6:
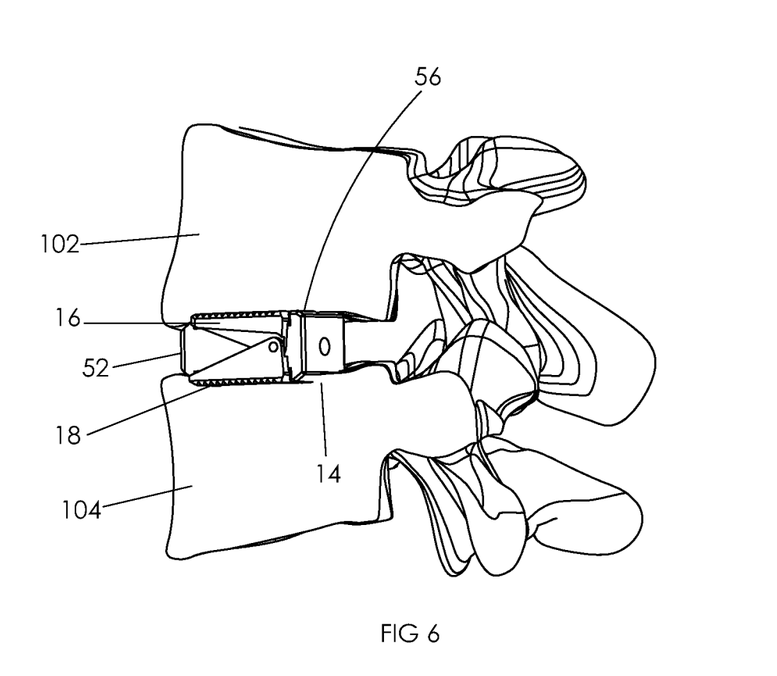
FIG. 6 is a pictorial view of the insert body to be inserted into the distractor.
Figure 7:
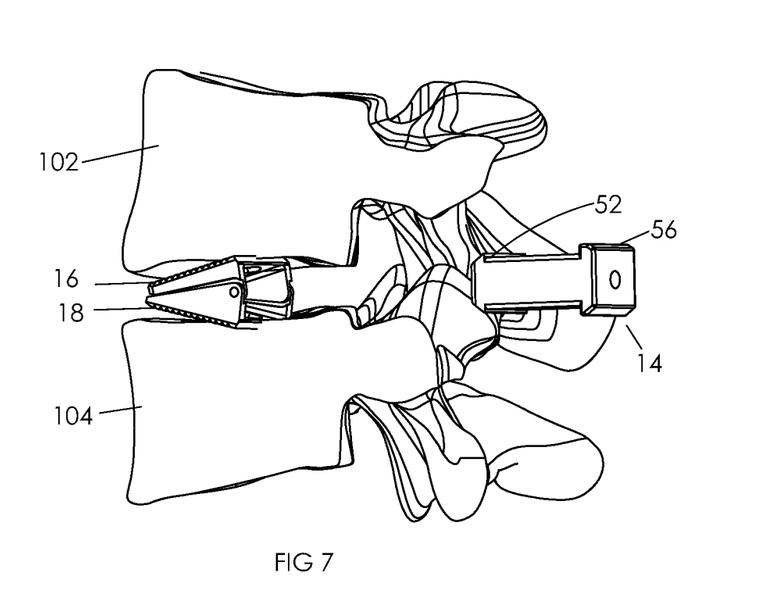
FIG. 7 is a pictorial view of the spinal implant installed.

FIGS. 6 and 7 are pictorial views of the spinal implant in position for placement between vertebra 102 and 104 with hinged distractor, formed from the upper support body 16 and lower support body 18, placed into position. Insert body 14 having leading edge 52 is slidably inserted between the upper and lower support bodies 16, 18 until the leading edge 52 and rear trailing edge 56 is locked into position. The upper surface 24 of the upper body and the outer surface of the lower body include contact lands and grooves 26 & 36 to frictionally engage the vertebral body. The distractor 12 is inserted between adjacent vertebrae, and the insert body 14 is placed into position, providing a desired distance between the bodies. The adjacent vertebrae are forced apart to equal the height of the implant. The spinal fusion device may be used unilaterally or bilaterally.

Referring now to FIGS. 8-12, disclosed is an implant 100 formed from a hinged distractor 102 and an insert body 104. The hinged distractor 102 is defined by a lower support body 106 and an upper support body 108 hinged together by use of pinions 120 and 122 insertable into slotted apertures 123 and 125.

The spinal implant upper support body 108 is constructed from a first upper section 111 having a proximal end 112 with a first upwardly facing pinion and distal end 114 with an upwardly facing pinion 115 with the slotted aperture 123 formed along a depending leg 116, and a second upper section 126 having a proximal end 127 with slotted aperture 128 and distal end 129 with slotted aperture 130. Slotted aperture 128 is for receipt of the upwardly facing pinion 113 and slotted aperture 130 is for receipt of the upwardly facing pinion 115. The second upper section further includes a depending leg 131 with slotted aperture 125.

The spinal implant lower support body 106 is constructed from a first lower section 140 having a proximal end 141 with downwardly facing pinion 142 and distal end 143 with downwardly facing pinion 144 with a first depending leg 145 having an outwardly depending pinion 122; and a second lower section 150 having a proximal end 151 with a slotted aperture 152 for receipt of said downwardly facing pinion 142 and a second slotted aperture 154 along distal end 153 for receipt of downwardly facing pinion 144. The second lower section 150 includes a depending leg 155 having an outwardly facing pinion 120 for engaging slotted aperture 123 of the first upper section 111.

The upper sections 111 and 126 of said upper support body 108 includes contact lands and grooves 160, 161 to provide a better purchase, although other stippled treatment may be employed. The upper support body 108 includes side walls 170 and 171 that are sloped from adjacent the dependent legs 116, 131 of proximal ends 112, 127 to the distal end 114, 129. The slope of the walls is further illustrated by a first height H1 adjacent the proximal end of the upper body 108 and a second height H2 adjacent the proximal end of the lower body 106. The combined height H3 of lower body 106 and upper body 108 dependent upon the size of the insertion body 104.

The lower support body 106 has an outer surface 180 which provides a large contact area with the vertebra. The outer surface 180 includes contact lands and grooves 180 to provide a better purchase, although other stippled treatment may be employed.

The upper support body 108 and lower support body 106 can may be made of conventional materials used for surgical implants, such as stainless steel and its many different alloys, titanium, and any other metal with the requisite strength and biologically inert properties. Polymeric materials with adequate strength and biological properties may also be used in the construction of the distractor.

Figure 8:
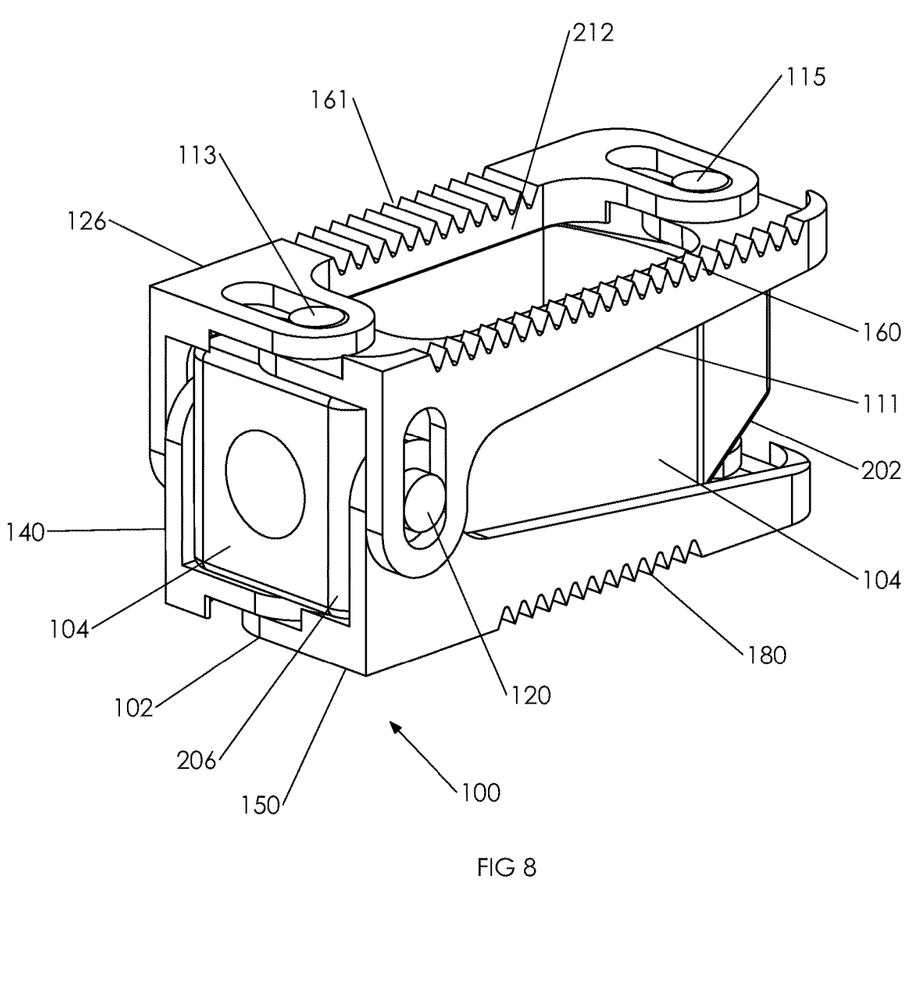
FIG. 8 is a perspective view of the spinal implant with two piece upper and lower sections.
Figure 9:
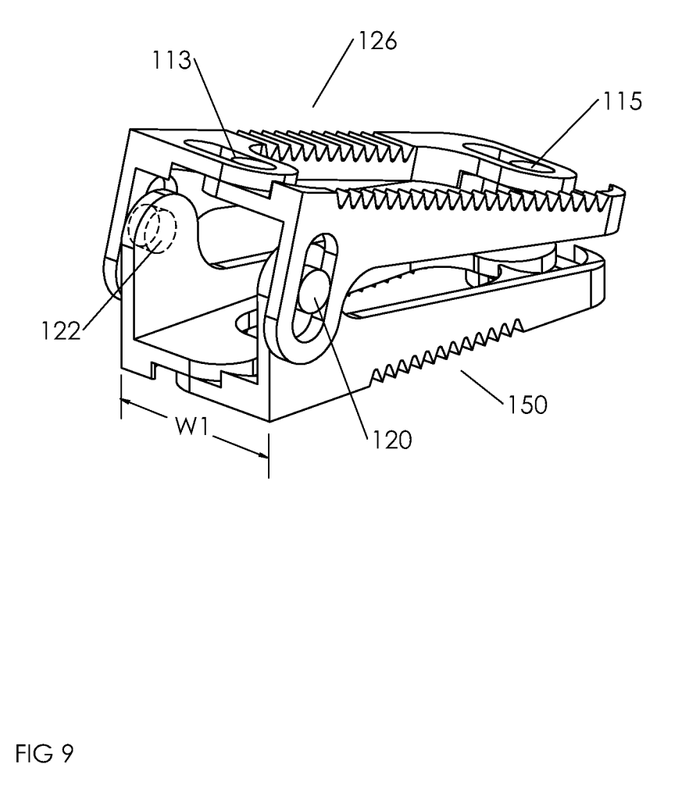
FIG. 9 is an exploded view of FIG. 8 with the upper and lower piece sections attached.
Figure 10:
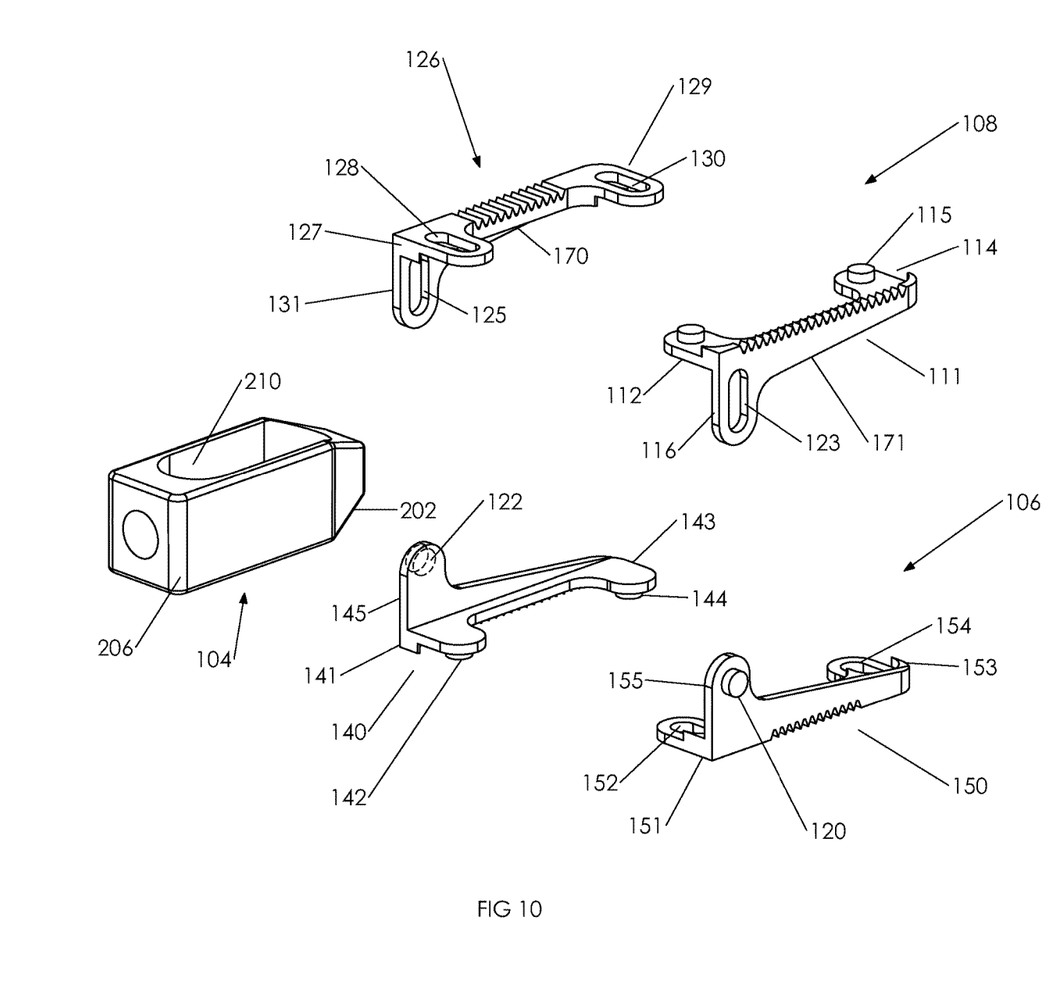
FIG. 10 is an exploded view of FIG. 8 with the upper and lower piece sections detached.
Figure 11:
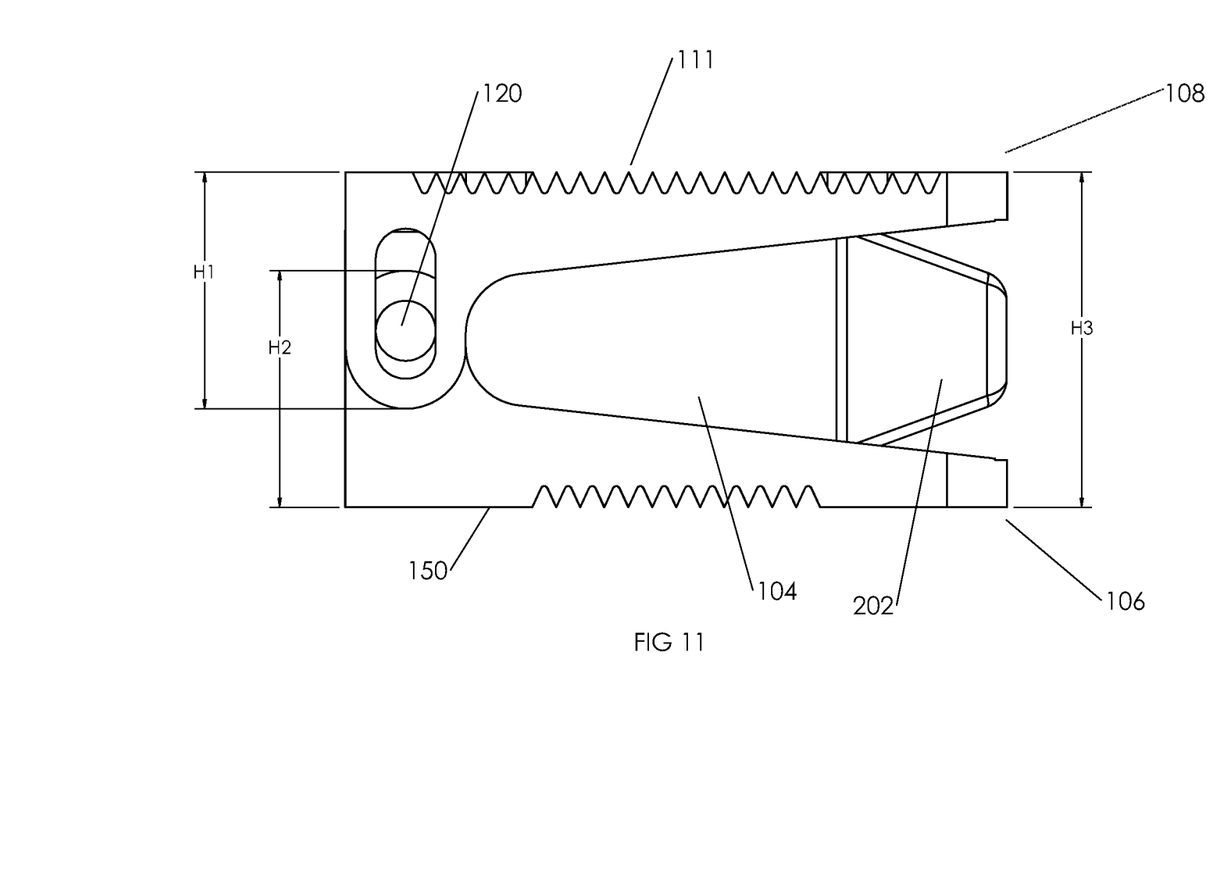
FIG. 11 is a side plane view thereof.

The insert body 104 is constructed and arranged to slide between the upper support body 108 and lower support body 106 to expand and maintain a space between the front edges proximal and distal ends of the distractor. The insert body 104 has a leading edge 202 that is tapered to allow ease of insertion with light tamping. A trailing edge 206 is shaped to fit within the distractor as illustrated in FIG. 8, wherein the trailing edge 206 is locked in position by the opening of the lower and upper support bodies 106, 108. The trailing edge 206 engages the rear edge of the upper and lower support sections to prevent the insert body from dislodging after installation.

Figure 12:
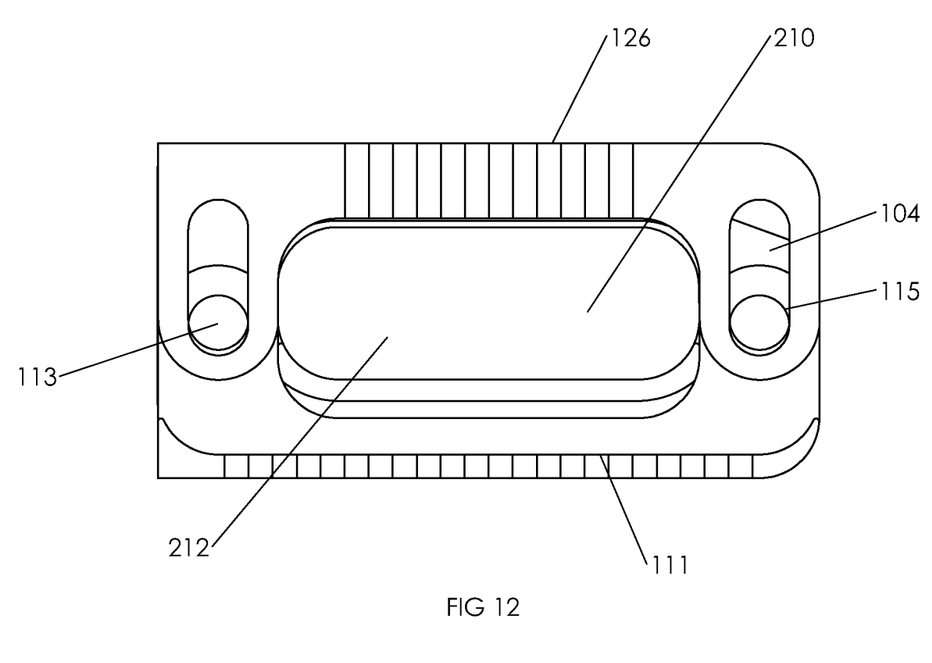
FIG. 12 is a top plane view thereof.

The insert body 104 is preferably constructed from polyether ether ketone (PEEK). The distractor and insert body are open as depicted in FIG. 12 to allow placement of bone growth material therein, or otherwise provide quicker fusion to the bone. Shown are aperture 210 and the insert body 104 having aperture 212.

In a similar manner as the previous embodiment, the spinal implant is positioned between vertebrae with the distractor formed from the upper support body 108 and lower support body 106 having two piece sections each having slotted apertures that expand in both a vertical and horizontal format upon placement of the insertion body 104. The insertion body 104, has a tapered leading edge 202 to allow the upper and lower support body to be first inserted in a compact position. Upon positioning of the upper and lower support body, the insertion body can be tapped into position causing expansion of each section in accordance with the limitations provided by the pinions and associated slotted apertures. The insertion body 104 is placed between the top and bottom support bodies that form the distractor, until the leading edge 202 and rear trailing edge 206 of the insert body are within the confines of the distractor. The tapered edges engaging the walls of the distractor to lock the distractor in position. The upper surface of the upper support body and the bottom surface of the lower support body includes lands and grooves to frictionally engage the vertebral body. Upon placing the insert body 104 into position, the height H3 and the width W2 are changed, providing a desired distance between the sections. The adjacent vertebrae are forced apart to equal the height of the implant, and the width spacing assures secure positioning. The spinal fusion device may be used unilaterally or bilaterally.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A spinal implant comprising:
   an upper support body composed of a first upper section member having a proximal end including a first upwardly facing pinion and a distal end having a second upwardly facing pinion with a slotted aperture formed along a depending leg, and
   a second upper section having a proximal end with a first slotted aperture for receipt of said first pinion and a distal end with a second slotted aperture for receipt of said second pinion and a slotted aperture formed along a depending leg; said upper section members combine to form a common upper surface and a lower surface with first and second sloped walls extending from the lower surface having a first height adjacent the proximal end tapering to a second height adjacent the distal end;
   a lower support body composed of a first lower section member having a proximal end with a first downwardly facing pinion and a distal end with a second downwardly facing pinion and a first outwardly extending pinion formed along a first depending leg for pivotedly coupling to said second slotted aperture of said second upper section, and
   a second lower section member having a proximal end with a slotted aperture for receipt of said downwardly facing pinion of said first lower section member and a second slotted aperture for receipt of said downwardly facing pinion of said first lower section distal end and a second outwardly extending pinion formed along a second depending leg for engaging said first slotted aperture of said first upper section, said lower section members combine to form a common outer surface and an inner surface with first and second sloped walls extending from the inner surface having a first height adjacent the proximal end tapering to a second height adjacent the distal end; and an insert body having a top surface, a bottom surface, opposing lateral sides, opposing anterior and posterior end walls and a substantially hollow center;

wherein said insert body is placed between said upper support body and said lower support body, whereby said upper body and said lower body expands in width and height to accommodate a width and height of said insert body.

2. The spinal implant according to claim 1 wherein said upper surface of said upper support body and said outer surface of said lower support body are stippled.

3. The spinal implant according to claim 1 wherein said upper surface of said upper support body and said outer surface of said lower support body includes contact lands and grooves.

4. The spinal implant according to claim 1 wherein said insert body includes a tapered leading edge for insertion between said upper and lower support bodies.

5. The spinal implant according to claim 1 wherein said insert body includes a trailing edge constructed and arranged to prohibit passage between said bodies.

6. The spinal implant according to claim 1 wherein said insert body is constructed from polyether ether ketone.

7. The spinal implant according to claim 5 wherein said first and second upper sections of said upper body form, and said first and second upper sections of said lower body form an aperture for receipt of bone growth material.

8. The spinal implant according to claim 1 wherein said insert body includes a centrally disposed aperture for receipt of bone growth material.

9. The spinal implant according to claim 1 wherein said hinged distractor and said insert body may be used unilaterally or bilaterally.

10. The spinal implant according to claim 1 wherein said insert body can be made from different widths and heights.

* * * * *